United States Patent [19]

Yellin et al.

[11] 4,332,949
[45] * Jun. 1, 1982

[54] 3-CHLOROALKYL-5-GUANIDINO-1,2,4-THIADIAZOLE COMPOUNDS

[75] Inventors: Tobias O. Yellin, Wallingford, Pa.; Derrick M. Mant, Bramhall, England

[73] Assignees: Imperial Chemical Industries PLC, London, England; ICI Americas Inc., Wilmington, Del.

[*] Notice: The portion of the term of this patent subsequent to Dec. 30, 1997, has been disclaimed.

[21] Appl. No.: 174,494

[22] Filed: Aug. 1, 1980

Related U.S. Application Data

[63] Continuation of Ser. No. 36,360, May 7, 1979, Pat. No. 4,242,350.

[30] Foreign Application Priority Data

May 24, 1978 [GB] United Kingdom ............... 21737/78

[51] Int. Cl.³ .......................................... C07D 285/08
[52] U.S. Cl. ................................................... 548/128
[58] Field of Search ......................................... 548/128

[56] References Cited

U.S. PATENT DOCUMENTS 4,242,350 12/1980 Yellin et al. ...................... 548/128

FOREIGN PATENT DOCUMENTS 916285 1/1963 United Kingdom .

Primary Examiner—Paul M. Coughlan, Jr.
Attorney, Agent, or Firm—David J. Levy; John M. Sheehan

[57] ABSTRACT

The invention relates to a thiadiazole derivative of the formula I:

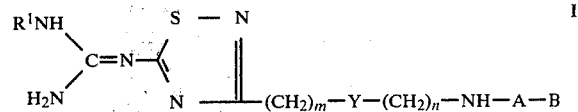

in which Y is O, S, $CH_2$, SO or a direct bond; m is 0 to 4 and n is 1 to 4 provided that when Y is S, O or SO m is 1 to 4, and when Y is O or SO n is 2 to 4; $R^1$ is H or $(C_{1-10})$alkyl; A is 3,4-dioxocyclobuten-1,2-diyl or C=Z in which Z is O, S, NCN, $NNO_2$, $CHNO_2$, $NCONH_2$, $C(CN)_2$, $NCOR^2$, $NCO_2R^2$, $NSO_2R^2$ or $NR^3$ in which $R^2$ is $(C_{1-6})$alkyl or $(C_{6-12})$aryl and $R^3$ is H or $(C_{1-6})$alkyl; B is $(C_{1-6})$alkoxy, $(C_{1-6})$alkylthio or $NR^4R^5$ in which $R^4$ and $R^5$ are independently H, $(C_{1-10})$alkyl, $C_{3-6}$(alkenyl), $(C_{3-6})$alkynyl, $(C_{2-6})$(primary hydroxy)alkyl, $(C_{2-6})$(primary amino)alkyl or $(C_{3-6})$cycloalkyl or $R^4$ and $R^5$ are joined to form a 5- or 6- membered saturated ring optionally containing an additional O or NH: and the salts thereof.

2 Claims, No Drawings

3-CHLOROALKYL-5-GUANIDINO-1,2,4-THIADIAZOLE COMPOUNDS

This is a continuation of application Ser. No. 036,360, filed May 7, 1979, now U.S. Pat. No. 4,242,350.

This invention relates to thiadiazole derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, Brit. J. Pharmac., 1966, 27, 427) and the action of histamine at this receptor is blocked (antagonised) by classical "antihistamine" drugs such as mepyramine. The second histamine receptor has been named the H-2 receptor (Black et al., Nature, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In U.K. Pat. Nos. 1,338,169 and 1,397,436 there are described histamine H-2 receptor antagonists which are heterocyclic derivatives having a side chain to the end of which is attached, for example, a urea, thiourea, guanidine or N-cyanoguanidine. It has now been discovered that if a guanidino radical is substituted in the 5-position of a 1,2,4-thiadiazole ring carrying such a side chain in the 3-position there are produced compounds which are potent histamine H-2 receptor antagonists.

According to the invention there is provided a thiadiazole derivative of the formula I:

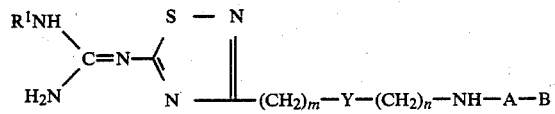

in which

Y is an oxygen or sulphur atom, a direct bond or a methylene or sulphinyl radical;

m is 0 to 4 and n is 1 to 4, provided that when Y is a sulphur or oxygen atom or a sulphinyl radical m is 1 to 4, and when Y is an oxygen atom or a sulphinyl radical n is 2 to 4, $R^1$ is a hydrogen atom or an alkyl radical of 1 to 10 carbon atoms;

A is a 3,4-dioxocyclobuten-1,2-diyl radical or a radical of the formula C=Z in which Z is an oxygen or a sulphur atom or a radical of the formula NCN, $NNO_2$, $CHNO_2$, $NCONH_2$, $C(CN)_2$, $NCOR^2$, $NCO_2R^2$, $NSO_2R^2$ or $NR^3$ in which $R^2$ is an alkyl radical of 1 to 6 carbon atoms or an aryl radical of 6 to 12 carbon atoms and $R^3$ is a hydrogen atom or an alkyl radical of 1 to 6 carbon atoms;

B is an alkoxy or alkylthio radical of 1 to 6 carbon atoms or a radical of the formula $NR^4R^5$ in which $R^4$ and $R^5$, which may be the same or different, are hydrogen atoms, alkyl radicals of 1 to 10 carbon atoms, alkenyl or alkynyl radicals of 3 to 6 carbon atoms in which the double or triple bond respectively is separated from the nitrogen atom of $NR^4R^5$ by at least one carbon atom, (primary hydroxy)alkyl or (primary amino)alkyl radicals of 2 to 6 carbon atoms or cycloalkyl radicals of 3 to 6 carbon atoms, or $R^4$ and $R^5$ are joined to form, together with the nitrogen atom to which they are attached, a 5- or 6-membered saturated ring which optionally contains an additional oxygen atom or NH radical; and the pharmaceutically-acceptable acid-addition salts thereof.

It is to be understood that, in the above formula I and throughout this specification, although the double bonds in both side chains have been inserted in particular positions, various other tautomeric forms are possible, and this invention includes such tautomeric forms within its scope, both in terms of the compound of the invention and in terms of the manufacturing processes.

A particular value for $R^1$ when it is an alkyl radical is a methyl radical.

A particular value for $R^2$ is a methyl or p-tolyl radical.

A particular value for $R^3$ is a methyl radical,

A particular value for B when it is an alkoxy or alkylthio radical is a methoxy, ethoxy or methylthio radical.

A particular value for $R^4$ or $R^5$ when it is an alkyl, alkenyl, alkynyl, (primary hydroxy)alkyl, (primary amino)alkyl or cycloalkyl radical is a methyl, ethyl, allyl, propargyl, 2-hydroxyethyl, 2-aminoethyl or cyclopropyl radical.

A particular value for the ring formed when $R^4$ and $R^5$ are joined is a pyrrolidine, piperidine, piperazine or morpholine ring.

The following are 7 preferred features of the thiadiazole derivative of the formula I. When any one of these features is taken, either singly or in combination, with the other general features of the thiadiazole derivative of the formula I listed above, there are obtained preferred sub-groups of compounds within the above general definition.

1. Y is a sulphur atom.
2. $R^1$ is a hydrogen atom.
3. B is a radical of the formula $NR^4R^5$ in which $R^5$ is a hydrogen atom.
4. B is an alkoxy or alkylthio radical.
5. A is a 3,4-dioxocyclobuten-1,2-diyl radical or a radical of the formula C=Z in which Z is a sulphur atom or a radical of the formula NCN, $NNO_2$, $CHNO_2$, $NCONH_2$ or $NSO_2CH_3$.
6. m is 1 and n is 2.
7. B is a radical of the formula $NR^4R^5$ in which $R^4$ is a hydrogen atom or a methyl radical and $R^5$ is a hydrogen atom.

Specific compounds of the invention are set out in the Examples.

The following is a preferred group of compounds:
3-[2-(3-cyano-2-methylisothioureido)ethylthiomethyl]-5-guanidino-1,2,4-thiadiazole;
3-[2-(2-cyano-3-methylguanidino)ethylthiomethyl]-5-guanidino-1,2,4-thiadiazole;
3-[2-(2-cyano-3-ethylguanidino)ethylthiomethyl]-5-guanidino-1,2,4-thiadiazole;
3-[2-(2-cyano-3-[2-hydroxyethyl]guanidino)ethylthiomethyl]-5-guanidino-1,2,4-thiadiazole;
3-[2-(2-nitroguanidino)ethylthiomethyl]-5-guanidino-1,2,4-thiadiazole;
3-[2-(3-methylthioureido)ethylthiomethyl]-5-guanidino-1,2,4-thiadiazole;
1-(2-[(5-guanidino-1,2,4-thiadiazol-3-yl)methylthio]ethylamino)-1-methylamino-2-nitroethylene;

3-[2-(2-cyano-3-[2-aminoethyl]guanidino)ethylthiomethyl]-5-guanidino-1,2,4-thiadiazole;

3-[2-(2-cyanoguanidino)ethylthiomethyl]-5-guanidino-1,2,4-thiadiazole;

and the pharmaceutically-acceptable acid-addition salts thereof.

A suitable pharmaceutically-acceptable acid-addition salt of the thiadiazole derivative of the invention is, for example, a salt formed with hydrochloric, hydrobromic, phosphoric, sulphuric, citric or maleic acid.

The thiadiazole derivative of the invention may be manufactured by methods known in themselves for the manufacture of chemically analogous compounds. Thus the following processes, Y, Z, m, n, A, B, $R^1$, $R^2$, $R^3$, $R^4$ and $R^5$ having the meanings stated above unless indicated otherwise, are provided as further features of the invention.

The process of the invention is characterized by:

(a) reaction of a compound of the formula II:

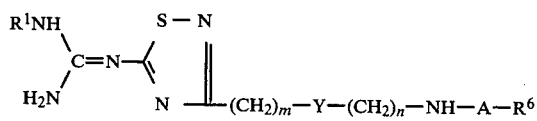

in which $R^6$ is a displaceable radical with a compound of the formula B—H;

(b) for those compounds in which A is a radical of the formula C=Z in which Z is a sulphur or oxygen atom and B is a radical of the formula $NR^4R^5$ in which $R^4$ is a hydrogen atom or an alkyl, alkenyl, alkynyl or cycloalkyl radical and $R^5$ is a hydrogen atom, reaction of a compound of the formula III:

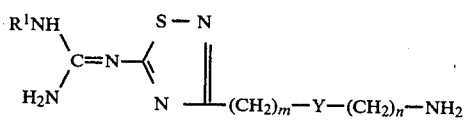

with a compound of the formula $R^7$—N=C=D in which $R^7$ is a hydrogen atom, an alkyl radical of 1 to 10 carbon atoms, an alkenyl or alkynyl radical of 3 to 6 carbon atoms in which the double or triple bond respectively is separated from the nitrogen atom of N=C=D by at least one carbon atom, or a cycloalkyl radical of 3 to 6 carbon atoms and D is a sulphur or oxygen atom;

(c) reaction of a compound of the formula III with a compound of the formula IV:

 IV in which $R^6$ is a displaceable radical;

(d) for those compounds in which A is a radical of the formula C=Z in which Z is a radical of the formula $NCONH_2$ and B is a radical of the formula $NR^4R^5$, hydrolysis of a compound of the formula I in which A is a radical of the formula C=Z in which Z is a radical of the formula NCN and B is a radical of the formula $NR^4R^5$;

(e) for those compounds in which Y is a sulphinyl radical, oxidation of a compound of the formula I in which Y is a sulphur atom.

When the process of the invention manufactures the compound of the formula I in the form of the free base and an acid-addition salt is required, the compound of the formula I in the free base form is reacted with an acid which affords a pharmaceutically-acceptable anion.

Process (a) may be carried out using an excess of B—H, that is using an excess of the amine $R^4R^5NH$, optionally in the presence of a diluent or solvent such as water, methanol, ethanol or pyridine, or using an excess of the compound $R^8$—OH or $R^8$—SH in which $R^8$ is an alkyl radical of 1 to 6 carbon atoms, preferably in the form of a salt such as the sodium salt in the same alcohol or thiol as diluent or solvent, $R^6$ may, for example, be an alkoxy or alkylthio radical of 1 to 6 carbon atoms, for example a methoxy, ethoxy or methylthio radical. The process may be accelerated or completed by the application of heat, for example by heating to the boiling point of the diluent or solvent.

Process (b) may be carried out using an excess of the isocyanate or isothiocyanate $R^7$—N=C=D. When D is a sulphur atom, the reaction is preferably carried out in a diluent or solvent such as methanol or ethanol. When D is an oxygen atom, a non-alcoholic diluent or solvent must be used. The process may be accelerated or completed by the application of heat, for example by heating to the boiling point of the diluent or solvent.

Process (c) may be carried out using an excess of the compound of the formula IV in a diluent or solvent such as methanol, ethanol or acetonitrile, $R^6$ may, for example, be an alkoxy or alkylthio radical of 1 to 6 carbon atoms, for example a methoxy, ethoxy or methylthio radical. The reaction may be accelerated or completed by the application of heat, for example by heating to the boiling point of the diluent or solvent.

Process (d) may be carried out using a dilute mineral acid, for example dilute hydrochloric acid, in a diluent or solvent such as water. The reaction may be accelerated or completed by an application of heat, for example by heating to the boiling point of the diluent or solvent.

Process (e) may be carried out using a mild oxidising agent such as sodium metaperiodate in a diluent or solvent such as aqueous methanol or aqueous ethanol.

When Y is an oxygen or sulphur atom and $R^1$ is H, the starting material of the formula III for use in process (b) or (c) may be prepared by reaction of a compound of the formula V:

 V with trichloromethanesulphenyl chloride followed by reaction of the product, the compound of the formula VI:

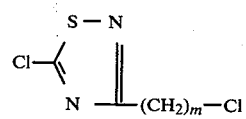 VI with a compound of the formula VII:

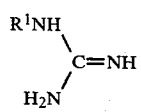 VII

The product from this reaction is then reacted with a compound of the formula VIII:

$$HD-(CH_2)_n-NH_2 \qquad \text{VIII}$$

in which D is an oxygen or sulphur atom to give the compound of the formula III. This sequence of reactions is illustrated in Examples 1 and 2.

When Y is a direct bond or a methylene radical, the starting material of the formula III for use in process (b) or (c) may be prepared by reaction of a compound of the formula IX:

$$H_2N-\overset{NH}{\overset{\|}{C}}-(CH_2)_m-X-(CH_2)_n-NHR^9 \qquad \text{IX}$$

in which X is a direct bond or a methylene radical and $R^9$ is a nitrogen protecting group with trichloromethanesulphenyl chloride followed by reaction of the product with the compound of the formula VII. The final stage in this procedure is thus removal of the protecting group $R^9$ to give the compound of the formula III.

When Y is a sulphinyl radical, the starting material of the formula III for use in process (b) or (c) may be obtained by oxidation of the compound of the formula III in which Y is a sulphur atom.

The starting material of the formula II for use in process (a) may be prepared by reaction of a compound of the formula III with a compound of the formula X:

$$R^6-A-R^6 \qquad \text{X}$$

in which $R^6$ is a displaceable radical, for example an alkoxy or alkylthio radical, for example as set out in Example 1, 2, 9, 10, 12, 13 or 14.

As noted above, the thiadiazole derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastro-intestinal bleeding due to trauma, e.g. in man.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced increase in the level of cyclic AMP (in the presence of a phosphodiesterase inhibitor) in a free cell suspension obtained from canine gastric mucosa.

The guinea pig atrium test is carried out as follows:

A guinea pig right atrium is suspended at 1 g. tension (isometric) in a thermostatically-controlled (30° C.) tissue bath (25 ml.) containing oxygenated (95% $O_2$; 5% $CO_2$) Krebs-Hanseleit buffer (pH 7.4). The tissue is allowed to stabilise over 1 hour during which time it is washed 2-4 times. Individual contractions are recorded with a force-displacement transducer through a strain gauge coupler, and instantaneous rates are monitored with a cardiotachometer. A control response to 1 µM histamine is obtained after which the tissue is washed 3 times and allowed to re-equilibrate to basal rate. After re-equilibration for 15 minutes, the test compound is added to the desired final concentration. Ten minutes after addition of the compound histamine (1 µM) is again added and the response to histamine in the presence of antagonist is compared to the histamine control response. The result is expressed as a percentage of the histamine control response. Thereafter the apparent dissociation constant of the H-2 antagonist is determined by standard procedures.

All the compounds exemplified in this specification are active on the guinea pig atrium test at or below a bath concentration of 10 µM., and the more active compounds show complete inhibition of response at this concentration.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, cats or dogs provided with gastric fistulae and whose gastric secretion is stimulated by the administration of a secretagogue, for example pentagastrin or histamine.

The test in dogs is carried out as follows:

A female pure bred beagle (9-12 kg.) having a chronic gastric fistula is fasted overnight with water ad lib. During the experiment the dog is lightly restrained in a standing position. When studying the test compound by the intravenous route, the fistula is opened and, after ascertaining the absence of basal secretion over a period of 30 minutes, a continuous intravenous infusion of secretagogue (0.5 µmole/kg/hour of histamine or 2 µg./kg./hour pentagastrin) in saline (15 ml./hour) is begun. Gastric acid samples are collected every 15 minutes. The volume of each sample is measured and a 1 ml. aliquot is titrated to neutrality with 0.1 NNaOH to determine acid concentration. When a plateau of secretion is reached, (1-2 hours) the test compound is administered intravenously in saline and gastric acid samples are collected for a further 2-3 hours during which time the infusion of the secretagogue continues uninterrupted.

When studying the test compound by the intragastric route, the absence of basal secretion over a period of 30 minutes is ascertained and the test compound, contained in 25 ml. of 0.5% w/v hydroxypropyl methylcellulose and 0.1% w/v 'Tween' 80 in water ('Tween' is a Trade Mark), is instilled into the stomach through a fistula dosing plug. One hour later, the fistula is reopened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route, it is administered in a gelatin capsule washed down with 15 ml. of water. One hour later, the fistula is opened and intravenous infusion of the secretagogue is immediately begun. Gastric acid samples are measured as above and the approach of acid secretion to a plateau is compared to that of an undosed control animal.

The results obtained in the atrium test are predictive of activity in the dog test.

No overt toxicity or side effects were noted during the dog tests. The compound 3-[2-(2-cyano-3-methylguanidino)ethylthiomethyl]-5-guanidino-1,2,4-thiadiazole showed no toxicity when dosed orally to rodents at 300 mg/kg. The same compounds was well tolerated in dogs dosed orally with 100 mg./kg.

According to a further feature of the invention there is provided a pharmaceutical composition which comprises a thiadiazole derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspensions, emulsions, dispersible powders, suppositories, sterile injectable aqueous or oily solutions or suspensions, gels, creams, ointments or lotions.

In addition to the thiadiazole derivative of the formula I, the pharmaceutical composition of the invention for oral, rectal or parenteral administration may also contain, or be co-administered with, one or more kown drugs selected from antacids, for example aluminum hydroxide-magnesium hydroxide mixtures; antipepsin compounds, for example pepstatin; other histamine H-2 antagonists, for example cimetidine; ulcer healing agents, for example carbenoxolone or bismuth salts; anti-inflammatory agents, for example ibuprofen, indomethacin, naproxen or aspirin; prostaglandins, for example 16,16-dimethylprostaglandin E$_2$; classical antihistamines (histamine H-1 antagonists), for example mepyramine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the thiadiazole derivative, one or more classical antihistamines (histamine H-1 antagonists), for example mepyramine or diphenhydramine and/or one or more steroidal anti-inflammatory agents, for example fluocinolone or triamcinolone.

A topical formulation may contain 1–10% w/w of the thiadiazole derivative of the invention. A preferred pharmaceutical composition of the invention is one suitable for oral administration in unit dosage form, for example a tablet or capsule which contains between 10 mg. and 500 mg. of the thiadiazole derivative, or one suitable for intravenous, subcutaneous or intramuscular injection, for example a sterile injectable containing between 0.1% and 10% w/w of the thiadiazole derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency of the thiadiazole derivative of the present invention relative to cimetidine. Thus each patient will receive an oral dose of between 15 mg. and 1500 mg. and preferably between 20 mg. and 200 mg. of thiadiazole derivative or an intravenous, subcutaneous or intramuscular dose of between 1.5 mg. and 150 mg., and preferably between 5 mg. and 20 mg. of the thiadiazole derivative, the composition being administered 2 to 4 times per day. The rectal dose will be approximately the same as the oral dose. The composition may be administered less frequently when it contains an amount of thiadiazole derivative which is a multiple of the amount which is effective when given 2–4 times per day.

Any of the well-known suitable pharmaceutical carriers can be used to prepare acceptable dosage forms so as to provide an effective amount or therapeutically effective amount of the compound to be administered.

| Tablet Containing 15 mg. of 3-[2-(3-cyano-2-methylisothioureido)ethylthiomethyl]-5-guanidino-1,2,4-thiadiazole | 1000 Tablets (Grams) |
| --- | --- |
| 3-[2-(3-cyano-2-methylisothioureido)ethylthiomethyl]-5-guanidino-1,2,4-thiadiazole | 15 |
| Starch | 102 |
| Powdered Lactose | 102 |
| Talc | 26 |
| Weight of Granulation | 245 |

Combine all ingredients, mix, and then compress into slugs. The slugs should then be ground to form granules that will pass through a 14 to 16 mesh screen. The granules may then be recompressed into tablets using a suitable compression mold to form tablets, each weighing 280 mg.

| Capsule Containing 100 mg. 3-[2-(3-cyano-2-methylisothioureido)ethylthiomethyl]-5-guanidino-1,2,4-thiadiazole | |
| --- | --- |
| 3-[2-(3-cyano-2-methylisothioureido)ethylthiomethyl]-5-guanidino-1,2,4-thiadiazole | 100 mg. |
| Powdered Lactose | 200 mg. |
| D.T.D. Capsules No. 1000 | |

Mix the ingredients so as to evenly distribute the active ingredient throughout the lactose. Pack the powder into a No. 1 empty gelatin capsule.

The invention is illustrated, but not limited by the following Examples in which the temperatures are in degrees centigrade:

EXAMPLE 1

A solution of crude 3-[(2-aminoethyl)thiomethyl]-5-guanidino-1,2,4-thiadiazole oxalate (6 g.) in water (180 ml.), triethylamine (2.1 ml.) and a solution of dimethyl (cyanoimido)dithiocarbonate (2.7 g.) in ethanol (180 ml.) was stirred at 70° for 1.5 hours. The solvent was evaporated in vacuo and the resulting oil was extracted with boiling ethanol (200 ml.). An excess of oxalic acid in ethanol was added to the extract which was then evaporated in vacuo to give a red oil which crystallised upon trituration with water (40 ml.). The crystals were filtered off and dried to give 3-[2-(3-cyano-2-methylisothioureido)ethylthiomethyl]-5-guanidino-1,2,4-thiadiazole oxalate.

The 3-[(2-aminoethyl)thiomethyl]-5-guanidino-1,2,4-thiadiazole oxalate used as starting material may be prepared as follows:

5-Chloro-3-chloromethyl-1,2,4-thiadiazole(b.p. 54°/2 m.m.) was prepared from chloroacetamidine and trichloromethanesulphenyl chloride by the procedure described by Goerdeler (*Chem.Ber.*, 1957, 90, 182) for the preparation of 5-chloro-3-methyl-1,2,4-thiadiazole.

Sodium hydride (4.8 g. of a 50% w/w dispersion in oil) washed free of oil with dried petroleum ether (b.p. 100°–120°) was stirred and warmed with dry t-butanol (200 ml.) for 30 minutes until gas evolution ceased. Guanidine hydrochloride (9.6 g.) was added followed after 10 minutes by 5-chloro-3-chloromethyl-1,2,4-thiadiazole (8.5 g.) and the resulting slurry was stirred for 20 minutes. The solid was removed from the resulting suspension by centrifugation to give a solution of crude 3-chloromethyl-5-guanidino-1,2,4-thiadiazole. Sodium methoxide (5.8 g.) was dissolved in magnesium-dried ethanol (100 ml.) and cooled to 10° under argon. 2-Aminoethanethiol hydrochloride (6 g.) was added, the mixture was stirred for 10 minutes and cooled to 5°. The t-butanol solution of 3-chloromethyl-5-guanidino-1,2,4-thiadiazole was added over 10 minutes with external cooling so that the temperature did not rise above 15°. After 30 minutes the solid precipitate was filtered off and the filtrate was acidified with a solution of oxalic acid in ethanol until no more solid was precipitated. The solid, 3-[(2-aminoethyl)thiomethyl]-5-guanidino-1,2,4-thiadiazole oxalate was filtered off, washed with a little ethanol and dried.

EXAMPLE 2

A mixture of 3-[2-(3-cyano-2-methylisothioureido)-ethylthiomethyl]-5-guanidino-1,2,4-thiadiazole (2.0 g.) and a 33% w/v solution of methylamine in ethanol (80 ml.) was stirred at 20° for 18 hours. The reaction mixture was filtered and the filtrate was evaporated in vacuo to an oil which was chromatographed on a silica column eluted with ethanol/toluene 1:2 v/v. The product, 3-[2-(2-cyano-3-methylguanidino)ethylthiomethyl]-5-guanidino-1,2,4-thiadiazole, had m.p. 159°–161° and an $R_f$ value of 0.4 on a Merck 60 F-254 plate developed with ethanol/toluene 1:2 v/v.

The n.m.r. spectrum in $d_6$ dimethyl sulphoxide using tetramethylsilane as an internal standard ($\delta=0$) had the following resonances ($\delta$):–7.2 (6H, multiplet); 3.7 (2H, singlet); 3.35 (2H, multiplet) and 2.7 (5H, multiplet).

EXAMPLE 3

A mixture of 3-chloromethyl-5-guanidino-1,2,4-thiadiazole (19.1 g.) and 2-aminoethanethiol hydrochloride (11.4 g.) was stirred in ethanol (200 ml.). 10.8 N NaOH (20 ml.) was added and the mixture was stirred for 2 hours. The precipitated solid was filtered off and washed with ethanol (200 ml.) and the combined filtrates were treated with dimethyl (cyanoimido)-dithiocarbonate (17.6 g.). After 10 minutes the product began to precipitate. After 1 hour the solid was filtered off, washed with ethanol and dried at 25°/0.2 m.m. to give 3-[2-(3-cyano-2-methylisothioureido)ethylthiomethyl]-5-guanidino-1,2,4-thiadiazole, m.p. 178°–179° (decomp.).

A suspension of 3-[2-(3-cyano-2-methylisothioureido)-ethylthiomethyl]-5-guanidino-1,2,4-thiadiazole (10 g.) in ethanol (200 ml.) was stirred and cooled to 10° with external ice cooling. Methylamine (166 g.) was passed into the suspension over 2 hours at such a rate that the temperature did not rise above 17° with external ice cooling. After 80 g. had been added, all was in solution. After 4 hours the ice bath was removed and excess methylamine was allowed to evaporate overnight. The final volume was about 120 ml. The product was filtered off, washed with a little ethanol, sucked dry and dried at 60°/0.3 m.m. Recrystallisation from aqueous ethanol (1:3 v/v) gave 3-[2-(2-cyano-3-methylguanidino)-ethylthiomethyl]-5-guanidino-1,2,4-thiadiazole, m.p. 198°–199°.

The 3-chloromethyl-5-guanidino-1,2,4-thiadiazole used as starting material may be obtained as follows:

Guanidine nitrate (244 g.) was slurried in dimethylformamide (500 ml., dried over molecular sieve) and sodium hydride paste (58 g. of a 63% w/w dispersion in oil) was added over 30 minutes with external cooling in an acetone/solid $CO_2$ bath to maintain the internal temperature at 25°–30°. The mixture was stirred for 30 minutes at 25° then cooled to 20°. 5-Chloro-3-chloromethyl-1,2,4-thiadiazole (84.5 g.) was added at 20°–25° over 20 minutes with external cooling at 5°–10°. The mixture was stirred for 20 minutes at 25° then poured into water (5000 ml.) and extracted with ethyl acetate (2×5000 ml.). The combined upper layers were extracted with 2 N HCl (2×500 ml.) and the combined acid extracts were basified with 2 N NaOH. The product was filtered off, washed with water, sucked dry and then dried over $P_2O_5$ at 1 m.m. to give 3-chloromethyl-5-guanidino-1,2,4-thiadiazole.

EXAMPLE 4

By a similar procedure to that described in the second part of Example 3, but using aqueous ethylamine (70% w/v) in place of methylamine there was prepared 3-[2-(2-cyano-3-ethylguanidino)ethylthiomethyl]-5-guanidino-1,2,4-thiadiazole, isolated as the salt with 1 molecule of oxalic acid, m.p. 139°–140°.

EXAMPLE 5

The process described in Example 4 was repeated using the appropriate amine in place of ethylamine and the following compounds were thus obtained:

$$\begin{array}{c} H_2N \\ \phantom{H_2N}\diagdown \\ \phantom{H_2NN}C=N- \\ \phantom{H_2N}\diagup \\ H_2N \end{array} \!\!\!\!\!\! \underset{N}{\overset{S-N}{\underset{\|}{\bigg\|}}} \!\!\!\! -CH_2-S-(CH_2)_2-NHC\overset{NCN}{\underset{\|}{\phantom{|}}}-NR^1R^2$$

| $NR^1R^2$ | Salt | m.p. |
|---|---|---|
| $NHCH_2CH_2OH$ | 1.5 oxalate | 126–128° |
| $NHCH_2CH_2NH_2$ | 1.66 oxalate . 0.5 ethanol | 142–144° |
| $NH_2$ | 1.25 oxalate . 0.5 ethanol | 137–139° |
| $N(CH_3)_2$ | free base | 159–161°* |
| ⟨N⟩ (piperidino) | free base . 0.25 ethanol | 178–179°* |

*Recystallised from ethanol

EXAMPLE 6

A mixture of 3-[-2-(2-cyano-3-methylguanidino)ethylthiomethyl]-5-guanidino-1,2,4-thiadiazole (0.2 g.) and 1 N hydrochloric acid (50 ml.) was heated under reflux for 30 minutes, cooled, neutralised with 1 N sodium hydroxide and extracted with ethyl acetate (6×25 ml.). The combined extracts were dried ($MgSO_4$) and evaporated in vacuo to a white solid which was dissolved in ethanol (3 ml.) and added to a solution of oxalic acid (0.071 g.) in ethanol (2 ml.). The precipitated solid was filtered off, washed with ethanol and dried at 50°/0.1 m.m. to give 3-[2-(2-carbamoyl-3-methylguanidino)ethylthiomethyl]-5-guanidino-1,2,4-thiadiazole. 1.75 oxalate. Found: C, 31.0; H, 4.3; N, 25.7; S, 13.5; $C_9H_{17}N_9OS_2.1.75\ C_2H_2O_4$ requires C, 30.7; H, 4.2; N, 25.8; S, 13.1%.

EXAMPLE 7

A solution of 3-[(2-aminoethyl)thiomethyl]-5-guanidino-1,2,4-thiadiazole (0.914 g.) in ethanol (10 ml.) was heated under reflux with methyl isothiocyanate (0.288 g.) for 20 minutes and the resulting solution was chromatographed on nine preparative Merck 60 F-254 silica plates (30 cm.×30 cm.) developed with toluene/ethanol/ethyl acetate/ammonia (s.g. 0.88) 60:40:20:10 v/v/v/v. The bands with an $R_f$ value of 0.6 were scraped off, extracted with ethanol and the extracts evaporated to a gum which crystallised on trituration with ethyl acetate to give 3-[2-(3-methylthioureido)ethylthiomethyl]-5-guanidino-1,2,4-thiadiazole. The n.m.r. spectrum in $d_6$ dimethyl sulphoxide using tetramethylsilane as an internal standard ($\delta=0$) had the following resonances ($\delta$): 2.76 (2H, triplet); 2.82 (3 H, singlet); 3.35 (2H, multiplet); 3.71 (2H, singlet); 7.12 and 7.5 (6 H, multiplets).

EXAMPLE 8

A solution of 3-[(2-(aminoethyl)thiomethyl]-5-guanidino-1,2,4-thiadiazole (0.6 g.) and 2-methyl-1-nitroisothiourea (0.35 g.) in ethanol (25 ml.) was kept overnight at ambient temperature. The precipitated solid was filtered off, washed with ethanol and dried at 40°/0.1 m.m. to give 3-[2-(2-nitroguanidino)ethylthiomethyl]-5-guanidino-1,2,4-thiadiazole, m.p. 184°–186°.

EXAMPLE 9

A solution of 3-[(2-aminoethyl)thiomethyl]-5-guanidino-1,2,4-thiadiazole (1.16 g.) and dimethyl (methylsulphonylimido)dithiocarbonate (1.0 g.) in ethanol (14 ml.) was stirred and a stream of argon was passed through it for 4 hours. The resulting solution was fractionated on seven preparative Merck 60F-254 silica plates (30 cm.×30 cm.) which were developed with toluene/ethanol/ethyl acetate/ammonia (s.g. 0.880) 60:40:20:10 v/v/v/v. The bands with $R_f$ values of 0.6 were extracted with ethanol, the combined extracts were evaporated to dryness and the resulting solid was recrystallised from ethyl acetate to give crude 3-[2-(2-methylsulphonyl-3-methylisothioureido)-ethylthiomethyl]-5-guanidino-1,2,4-thiadiazole, m.p. 120°–122°.

The above isothiourea (0.30 g.) was dissolved in a mixture of ethanol (9 ml.), water (6 ml.) and a solution of methylamine in ethanol (9 ml. of 33% w/v solution) and stirred for 24 hours at ambient temperature. The solution was evaporated in vacuo to an oil which was dissolved in hot ethanol (1.5 ml.) and cooled. There was thus obtained 3-[2-(2-methylsulphonyl-3-methylguanidino)ethylthiomethyl]-5-guanidino-1,2,4-thiadiazole, m.p. 172°–173°.

EXAMPLE 10

A solution of 3-[(2-aminoethyl)thiomethyl]-5-guanidino-1,2,4-thiadiazole (7.32 g.) and dimethyl (N-cyanoimido)carbonate (1.14 g.) in methanol (20 ml.) was kept at 25° for 20 hours. The resulting solution was fractionated on silica plates as in Example 9 ($R_f$ value 0.8) and finally isolated from ethanol with oxalic acid, to give 3-[2-(3-cyano-2-methylisoureidoethylthiomethyl]-5-guanidino-1,2,4-thiadiazole, m.p. 159°–161°.

EXAMPLE 11

A mixture of 3-[2-(2-cyano-3-methylguanidino)-ethylthiomethyl]-5-guanidino-1,2,4-thiadiazole (0.626 g.), sodium metaperiodate (0.428 g.), methanol (20 ml.) and water (70 ml.) was stirred overnight at room temperature. The reaction mixture was evaporated to dryness and the residue extracted with absolute ethanol (120 ml.). The extract was filtered and evaporated to dryness. The residue was crystallised from methanol (with charcoal treatment) to give 3-[2-(2-cyano-3-methylguanidino)-ethylsulphinylmethyl]-5-guanidino-1,2,4-thiadiazole as a white powder, m.p. 185°–186°.

EXAMPLE 12

A solution of sodium hydroxide (0.8 g.) in ethanol (3 ml.) and water (2.5 ml.) was added dropwise to a stirred mixture of 3-chloromethyl-5-guanidino-1,2,4-thiadiazole (1.91 g.) and 3-aminopropanethiol hydrochloride (1.28 g.) in ethanol (25 ml.) at room temperature under a nitrogen atmosphere. The resulting pale yellow suspension was stirred for 4.5 hours and allowed to stand overnight. It was then treated with charcoal and filtered through diatomaceous earth. Dimethyl (N-cyanoimido)dithiocarbonate (1.46 g.) was added to the filtrate and the mixture stirred at room temperature for 5 hours. This mixture was poured into water (50 ml.) and extracted with ethyl acetate (3×25 ml.). The combined organic extracts were washed with water (50 ml.), dried (magnesium sulphate), filtered and evaporated to dryness. The residual gum of 3-[3-(3-cyano-2-methylisothioureido)propylthiomethyl]-5-guanidino-1,2,4-thiadiazole was dissolved in ethanol (15 ml.) and treated with ethanolic methylamine (30 ml. of 30% w/v solution). The mixture was stirred at room temperature for 4 hours and left to stand for three days. The mixture was evaporated to dryness and the residue purified by preparative thin layer chromatography on Merck 60F-254 plates developed with ethyl acetate/ammonia (s.g. 0.88)/ethanol 6:1:1 v/v/v. The product was crystallised from aqueous acetone to give 3-[3-(3-cyano-2-methylguanidino)propylthiomethyl]-5-guanidino-1,2,4-thiadiazole as a white solid, m.p. 117°–120°.

EXAMPLE 13

A mixture of 3-[(2-aminoethyl)thiomethyl-5-guanidino-1,2,4-thiadiazole] (prepared from 3-chloromethyl-5-guanidino-1,2,4-thiadiazole (1.9 g.) as described in Example 3) in ethanol (20 ml.) and 1,1-di(-methylthio)-2-nitroethylene (1.65 g.) in methanol (50 ml.) was heated under reflux for 8 hours. The mixture was evaporated to dryness and the residue was extracted with hot ethanol (50 ml.). The ethanol solution was cooled, filtered and the filtrate evaporated to dryness. The residue was triturated with methanol (5 ml.) and the residue was crystallised from ethanol to give 1-(2-[(5-guanidino-1,2,4-thiadiazol-3-yl)methylthio]ethylamino)-1-methyl-thio-2-nitroethylene as a pale brown solid, (0.33 g.). This solid was added to a 30% w/v solution of methylamine in ethanol (10 ml.) and the mixture was stirred at 25° for 16 hours. The product was filtered and washed with ethanol (5 ml.) to give 1-(2-[(5-guanidino-1,2,4-thiadiazol-3-yl)methylthio]ethylamino)-1-methylamino-2-nitroethylene (0.16 g.), m.p. 152°–6° (decomp.).

EXAMPLE 14

To a solution of sodium ethoxide prepared from sodium hydride (50% w/w dispersion in oil; 0.384 g.) and ethanol (20 ml.) at 0° was added 2-aminoethanethiol hydrochloride (0.456 g.) and 3-chloromethyl-5-guanidino-1,2,4-thiadiazole (0.768 g.). The mixture was stirred at 0° and under an atmosphere of argon for 2 hours, and then allowed to stand at 4° for 3 days. The mixture was then filtered and added to a solution of 1,2-dimethoxycyclobutene-3,4-dione (0.568 g.) in dry methanol (10 ml.). The resulting yellow-orange solution was filtered and the filtrate evaporated to dryness and the residue triturated several times with dry petroleum ether (b.p. 60°–80°). The resulting crude gum, 1-(2-[(5-guanidino-1,2,4-thiadiazol-3-yl)methylthio]ethylamino)-2-methoxycyclobutene-3,4-dione, was then taken into a solution of methylamine in ethanol (33% w/v; 10 ml.) and stirred at room temperature overnight. The precipitated pale yellow solid was filtered off and air-dried to give 1-(2-[(5-guanidino-1,2,4-thiadiazol-3- yl)methylthio]ethylamino)-2-methylaminocyclobutene-3,4-dione (0.65 g.), m.p. 238°–239° (decomp.).

EXAMPLE 15

Pure 3-chloromethyl-5-guanidino-1,2,4-thiadiazole (150 g.) was stirred in ethanol (600 ml.) at 10° and 2-aminoethanethiol hydrochloride (93 g.) added. 18 N NaOH (92 ml.) diluted with water (300 ml.) was then added over 30 minutes at 10°–15°. After 90 minutes further water (600 ml.) was added and the solution was stirred for a further 30 minutes before dimethyl (N-cyanoimido)carbonate (107 g.) was added. The resulting solution was stirred for 60 minutes and then aqueous methylamine (40% w/w, 660 ml.) was added. The mixture was stirred for 18 hours and the product removed by filtration and washed with ethanol/water (1:1 v/v, 2×250 ml.) (164 g., 67%). Crystallisation from ethanol/water 3:1 v/v gave 3-[2-(2-cyano-3-methyl-guanidino)ethylthiomethyl]-5-guanidino-1,2,4-thiadiazole.

The pure 3-chloromethyl-5-guanidino-1,2,4-thiadiazole used as starting material may be obtained as follows:

Impure 3-chloromethyl-5-guanidino-1,2,4-thiadiazole (199 g.) was stirred in 2 N HCl (1 l.) for 1 hour). The pH was adjusted to 4 with 18 N NaOH and diatomaceous earth (60 g.) added. The mixture was stirred for 1 hour, activated carbon (40 g.) was added and the mixture was stirred for a further hour. The mixture was then filtered and the solid washed with 2 N HCl (2×80 ml.). The pH of the combined filtrates was adjusted to 8 with 18 N NaOH and the pure 3-chloromethyl-5-guanidino-1,2,4-thiadiazole was filtered and washed with water (157 g., 79%).

EXAMPLE 16

Methyl isocyanate (0.6 ml.) was added to a solution of 3-[(2-aminoethyl)thiomethyl]-5-guanidino-1,2,4-thiadiazole (2.3 g.) in dry tetrahydrofuran (5 ml.). After 16 hours the resulting solution was chromatographed on twenty silica GF 254 plates (40 cm.×20 cm.) developed with toluene/ethanol/ethyl acetate/ammonia (s.g. 0.88) 60:40:20:10 v/v/v/v and the fractions with an $R_f$ value of 0.5 were scraped off and extracted with ethanol. The ethanol extracts were added to a solution of oxalic acid (1.4 g.) in ethanol (50 ml.) and the resulting precipitate was filtered off and dried to give 3-[2-(3-methylureido)-ethylthiomethyl]-5-guanidino-1,2,4-thiadiazole mono oxalate, 0.3 ethanol, m.p. 169°–172°.

What we claim is:

1. A thiadiazole derivative of the following formula:

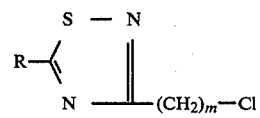

wherein
R is guanidino; and
m is 1 to 4.

2. The thiadiazole derivative of claim 1, wherein said derivative is 3-chloromethyl-5-guanidino-1,2,4-thiadiazole.

* * * * *